(12) United States Patent
Holloway

(10) Patent No.: US 6,921,807 B2
(45) Date of Patent: Jul. 26, 2005

(54) PROTEINASE INHIBITOR ZSERP9

(75) Inventor: James L. Holloway, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 2 days.

(21) Appl. No.: 10/113,113

(22) Filed: Mar. 29, 2002

(65) Prior Publication Data
US 2003/0166852 A1 Sep. 4, 2003

Related U.S. Application Data

(60) Provisional application No. 60/280,678, filed on Mar. 29, 2001.
(51) Int. Cl.$^7$ .......................... C07K 1/00; C07H 21/04; C12N 15/00; C12N 9/48; C12Q 1/00
(52) U.S. Cl. .......................... 530/350; 536/23.2; 435/4; 435/6; 435/212; 435/440
(58) Field of Search .......................... 530/350; 435/440, 435/6, 4, 212, 183; 536/23.1, 23.2

(56) References Cited

U.S. PATENT DOCUMENTS
6,583,269 B1 * 6/2003 Hu et al. .................... 530/350

FOREIGN PATENT DOCUMENTS
| WO | 01/81363 A1 | 11/2001 |
| WO | 02/072769 A2 | 9/2002 |

* cited by examiner

*Primary Examiner*—Manunath Rao
*Assistant Examiner*—Yong Pak
(74) *Attorney, Agent, or Firm*—Gary E. Parker

(57) ABSTRACT

A novel proteinase inhibitor and materials and methods for making it are disclosed. The proteinase inhibitor comprises residues 3–425 of SEQ ID NO:2. The proteinase inhibitor may be used as components of cell culture media, in protein purification, and in certain therapeutic and diagnostic applications.

4 Claims, No Drawings

US 6,921,807 B2

PROTEINASE INHIBITOR ZSERP9

CROSS-REFERENCE TO RELATED APPLICATION

This application claims priority under 35 U.S.C. § 119(e) from provisional application No. 60/280,678, filed Mar. 29, 2001.

BACKGROUND OF THE INVENTION

In animals, proteinases are important in wound healing, extracellular matrix destruction, tissue reorganization, and in cascades leading to blood coagulation, fibrinolysis, and complement activation. Proteinases are released by inflammatory cells for destruction of pathogens or foreign materials, and by normal and cancerous cells as they move through their surroundings. Overproduction or lack of regulation of proteinases can also have pathological consequences. Elastase, released within the lung in response to the presence of foreign particles, can damage lung tissue if its activity is not tightly regulated. Emphysema in smokers is believed to arise from an imbalance between elastase and its inhibitor, alpha-1-antitrypsin. This balance may be restored by administration of exogenous alpha-1-antitrypsin.

Proteinases are also used within a wide range of applications in industry and research. Through the use of proteinases and other enzymes, industrial processes can be carried out at reduced temperatures and pressures and with less dependence on the use of corrosive or toxic substances. The use of enzymes can thus reduce production costs, energy consumption, and pollution as compared to non-enzymatic products and processes. Industrial applications of proteinases include food processing, brewing, and alcohol production. Proteinases are important components of laundry detergents and other products. Within biological research, proteinases are used in purification processes to degrade unwanted proteins.

The activity of proteinases is regulated by inhibitors; 10% of the proteins in blood serum are proteinase inhibitors (Roberts et al., *Critical Reviews in Eukaryotic Gene Expression* 5:385–436, 1995). One family of proteinase inhibitors, the serpins (serine proteinase inhibitors), includes inhibitors of elastase, trypsin, chymotrypsin, thrombin, plasmin, and other proteinases. These inhibitors thus regulate a variety of physiological processes, including blood coagulation, fibrinolysis, complement activation, inflammation, and tumor development.

Proteinase inhibitors regulate the proteolytic activity of target proteinases by occupying the active site and thereby preventing occupation by normal substrates. The serpins possess an exposed loop (variously termed an "inhibitor loop", a "reactive core", a "reactive site", or a "binding loop") that is accessible to the target proteinase. Interaction between inhibitor and enzyme produces a stable complex which disassociates very slowly, releasing a modified inhibitor that is cleaved at the scissile bond of the binding loop (the $P_1$–$P_1'$ bond). See, Carrell et al., *Cold Spring Harbor Symp. Quant. Biol.* LII:527–535, 1987.

Serpins are characterized by a highly ordered, globular structure composed of pleated sheets and α helices. Although serpins share the same overall tertiary structure, they are quite diverse in sequence. Even closely related members of this family may be only about 30% identical in amino acid sequence (Carrell et al., ibid.). Inhibitory specificity is determined primarily by the identities of the amino acid residues in the $P_1$–$P_2$ positions.

One subfamily of serpins are structurally related to ovalbumin. These "ov-serpins" lack cleavable secretory peptides, and many function intracellularly. Some members of this subfamily are involved in the regulation of inflammation and apoptosis. This subfamily includes the interleukin-1β converting enzyme (ICE) inhibitor crmA from cowpox virus (Ray et al., *Cell* 69:597–604, 1992) and CAP-3 (Sprecher, U.S. Pat. No. 5,747,645). Some members of this subfamily, including ovalbumin, plasminogen activator inhibitor-2 (PAI-2), squamous cell carcinoma antigen (SCCA), and maspin, are efficiently secreted, apparently due to an internal secretion signal. PAI-2 may also function intracellularly. The intracellular Ov-serpins have been reviewed by Korpula-Mastalerz and Dubin (*Acta Biochim. Polonica* 43:419–430, 1996).

In view of the specificity of proteolytic enzymes and the growing use of proteinases in industry, research, and medicine, there is an ongoing need in the art for new enzymes and new enzyme inhibitors. The present invention addresses these needs and provides other, related advantages.

DESCRIPTION OF THE INVENTION

Within one aspect of the invention there is provided an isolated polypeptide comprising amino acid residues 3–425 of SEQ ID NO:2. Within one embodiment the polypeptide is not more than 1500 amino acid residues in length. Within another embodiment the polypeptide is not more than 1000 amino acid residues in length. Within a further embodiment the polypeptide is from 423 to 448 amino acid residues in length. Within additional embodiments the polypeptide comprises residues 2–425 of SEQ ID NO:2 or residues 1–425 of SEQ ID NO:2. Within other embodiments the polypeptide consists of residues 3–425 of SEQ ID NO:2, residues 2–425 of SEQ ID NO:2, or residues 1–425 of SEQ ID NO:2. Within further embodiments the polypeptide comprises an affinity tag. Within related embodiments the affinity tag is maltose binding protein, polyhistidine, or Glu-Tyr-Met-Pro-Met-Glu (SEQ ID NO:4).

Within a second aspect of the invention there is provided an expression vector comprising the following operably linked elements: (a) a transcription promoter; (b) a DNA segment encoding a polypeptide comprising amino acid residues 3–425 of SEQ ID NO:2; and (c) a transcription terminator. Within one embodiment the expression vector further comprises a secretory signal sequence operably linked to the DNA segment. Within another embodiment the polypeptide is from 423 to 448 amino acid residues in length. Within other embodiments the polypeptide is not more than 1500 amino acid residues in length or not more than 1000 amino acid residues in length. Within another embodiment the polypeptide comprises residues 2–425 of SEQ ID NO:2 or residues 1–425 of SEQ ID NO:2. Within other embodiments the polypeptide consists of residues 3–425 of SEQ ID NO:2, residues 2–425 of SEQ ID NO:2, or residues 1–425 of SEQ ID NO:2. Within a further embodiment the polypeptide further comprises an affinity tag. Within related embodiments the affinity tag is maltose binding protein, polyhistidine, or Glu-Tyr-Met-Pro-Met-Glu (SEQ ID NO:4).

Within a third aspect of the invention there is provided a cultured cell containing an expression vector as disclosed above, wherein the cell expresses the DNA segment.

Within a fourth aspect of the invention there is provided a method of making a polypeptide comprising culturing a cell as disclosed above under conditions whereby the DNA segment is expressed, and recovering the polypeptide encoded by the DNA segment. Within one embodiment the expression vector further comprises a secretory signal sequence operably linked to the DNA segment, and the polypeptide is secreted into and recovered from a culture medium in which the cell is cultured.

Within a fifth aspect of the invention there is provided a polypeptide produced by the method disclosed above.

Within a sixth aspect of the invention there are provided antibodies the specifically bind to the polypeptides disclosed above.

Within a seventh aspect of the invention there is provided a method of reducing proteolysis of a protein in a solution, wherein the method comprises adding to the solution an effective amount of a protein comprising residues 3–425 of SEQ ID NO:2.

These and other aspects of the invention will become evident upon reference to the following detailed description.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any polypeptide or protein for which an antibody or other specific binding agent is available can be used as an affinity tag. Affinity tags include a poly-histidine tract, protein A (Nilsson et al., $EMBO$ $J.$ 4:1075, 1985; Nilsson et al., $Methods$ $Enzymol.$ 198:3, 1991), glutathione S transferase (Smith and Johnson, $Gene$ 67:31, 1988), Glu-Glu affinity tag (Glu-Tyr-Met-Pro-Met-Glu; SEQ ID NO:4) (Grussenmeyer et al., $Proc.$ $Natl.$ $Acad.$ $Sci.$ $USA$ 82:7952–4, 1985), substance P, Flag™ peptide (Hopp et al., $Biotechnology$ 6:1204–10, 1988), streptavidin binding peptide, or other antigenic epitope or binding domain. See, in general, Ford et al., $Protein$ $Expression$ $and$ $Purification$ 2: 95–107, 1991. DNAs encoding affinity tags are available from commercial suppliers (e.g., Amersham Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used herein to denote a protein encoded by an allelic variant of a gene.

"Conservative amino acid substitutions" are defined by the BLOSUM62 scoring matrix of Henikoff and Henikoff, $Proc.$ $Natl.$ $Acad.$ $Sci.$ $USA$ 89:10915–10919, 1992, an amino acid substitution matrix derived from about 2,000 local multiple alignments of protein sequence segments, representing highly conserved regions of more than 500 groups of related proteins. As used herein, the term "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

An "inhibitory polynucleotide" is a DNA or RNA molecule that reduces or prevents expression (transcription or translation) of a second (target) polynucleotide. Inhibitory polynucleotides include antisense polynucleotides, ribozymes, and external guide sequences. The term "inhibitory polynucleotide" further includes DNA and RNA molecules that encode the actual inhibitory species, such as DNA molecules that encode ribozymes.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, $Nature$ 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polynucleotide, polypeptide, or protein obtained from one species that is the functional counterpart of a polynucleotide, polypeptide, or protein from a different species. Sequence differences among orthologs are the result of speciation.

A "polynucleotide" is a single- or double-stranded polymer of deoxyribonucleotide or ribonucleotide bases read from the 5' to the 3' end.

Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. Thus, a protein "consisting of," for example, from 15 to 1500 amino acid residues may further contain one or more carbohydrate chains.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based on the discovery of a novel protein having sequence homology to the serine proteinase inhibitor (serpin) family. A representative human amino acid sequence of this protein, which has been designated "zserp9," is shown in SEQ ID NO:2. Residues 3–425 of SEQ ID NO:2 exhibit a highly significant degree of sequence similarity to a serpin amino acid sequence profile. Zserp9 exhibits structural features of the ovalbumin subfamily of serpins, including a lack of the N- and C-terminal extensions seen in alpha-1 antitrypsin, the lack of a conventional, N-terminal secretory peptide, and a C-terminal Ser-Pro dipeptide. Zserp9 contains four alanine residues at $P_9$-$P_{12}$ (residues 379–382), which is characteristic of the inhibitory serpins. Residues 61 through 105 of SEQ ID NO:2 appear to be an insertion relative to the serpin profile, a feature that is also present in other ovserpins, including PAI-2 (Remold-O'Donnell, *FEBS Lett.* 315:105–108, 1993). Zserp9 contains 6 potential N-linked glycosylation sites, at residues 66, 107, 238, 309, 375, and 411 of SEQ ID NO:2.

From an alignment SEQ ID NO:2 with a serpin profile, residue 390 (Arg) is believed to be in the $P_1$ position, with a Ser in the $P_1'$ position. The predicted reactive center of zserp9 thus includes the same residues as the human thrombin inhibitors antithrombin III and alpha-1-antitrypsin Pittsburgh, suggesting that zserp9 inhibits preoteinases with thrombin-like specificity. This reactive center sequence further suggests that zserp9 also inhibits tissue-type plasminogen activator, urokinase, and factor Xa.

Analysis of SEQ ID NO:2 using Protean™ 3.14 software (DNAStar, Madison, Wis.) gives a calculated molecular weight of 48,419 and isoelectric point of 5.29 for the primary translation product.

Variants of the zserp9 sequence shown in SEQ ID NO:2 can be used to provide proteinase inhibitors having altered inhibitory activity (e.g., a different target proteinase or a quantitatively different activity) or to study the effects of amino acid changes on the properties of serpins. Such variant polypeptides comprise one or more amino acid substitutions, deletions, or insertions as compared to SEQ ID NO:2. The invention thus provides zserp9 variant proteins that are at least 80%, at least 85%, at least 90%, at least 95%, and at least 98% identical to residues 1–425 or residues 3–425 of SEQ ID NO:2.

Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as:

Total number of identical matches/ [length of the longer sequence plus the number of gaps introduced into the longer sequence in order to align the two sequences]×100

Thus, polypeptides of the present invention can be prepared with one or more amino acid substitutions, deletions or additions as compared to SEQ ID NO:2. These changes can be of a minor nature, that is conservative amino acid substitutions and other changes that do not significantly affect the folding or activity of the polypeptide, and include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20–25 residues, or an affinity tag as disclosed above. Two or more affinity tags may be used in combination. Polypeptides comprising affinity tags can further comprise a polypeptide linker and/or a proteolytic cleavage site between the zserp9 polypeptide and the affinity tag. Within certain embodiments of the invention one or more cysteine residues within SEQ ID NO:2 is deleted or replaced with another amino acid residue to limit improper folding.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

The present invention further provides a variety of other polypeptide fusions and related multimeric proteins comprising one or more polypeptide fusions. For example, a zserp9 polypeptide can be prepared as a fusion to a multimerizing protein as disclosed in U.S. Pat. Nos. 5,155,027 and 5,567,584. Exemplary multimerizing proteins in this regard include immunoglobulin constant region domains. Ig constant region domains may also be used to increase the circulatory half-life of fusion proteins comprising them. For example, a zserp9 polypeptide can be joined to an IgG Fc fragment (consisting essentially of $C_H2$, $C_H3$, and hinge). Such fusions are typically secreted as multimeric molecules wherein the Fc portions are disulfide bonded to each other and two non-Ig polypeptides are arrayed in close proximity to each other. Immunoglobulin-zserp9 polypeptide fusions can be expressed in genetically engineered cells to produce a variety of multimeric zserp9 analogs. Within immunoglobulin-zserp9 fusion proteins, certain amino acid subsititutions may be introduced into the Ig portion to alter effector functions associated with the native Ig. For example, amino acid substitutions can be made at EU index positions 234, 235, and 237 to reduce binding to FcγRI, and at EU index positions 330 and 331 to reduce complement fixation. See, Duncan et al., *Nature* 332:563–564, 1988; Winter et al., U.S. Pat. No. 5,624,821; Tao et al., *J. Exp. Med.* 178:661, 1993; and Canfield and Morrison, *J. Exp. Med.* 173:1483, 1991. The carboxyl-terminal lysine residue can be removed from the $C_H3$ domain to increase homogeneity of the product. Within fusions to an Ig heavy chain polypeptide, the Cys residue within the hinge region that is ordinarily disulfide-bonded to the light chain can be replaced with another amino acid residue, such as a serine residue, if the Ig fusion is not co-expressed with a light chain polypeptide. However, an Ig-zserp9 fusion polypeptide can be co-expressed with a wild-type or fused light chain polypeptide as disclosed in U.S. Pat. No. 6,018,026. Auxiliary domains can be fused to zserp9 polypeptides to target them to specific cells, tissues, or macromolecules (e.g., collagen). For example, a zserp9 polypeptide or protein can be targeted to a predetermined cell type by fusing a zserp9 polypeptide to a ligand that specifically binds to a receptor on the surface of the target cell. In this way, polypeptides and proteins can be targeted for therapeutic or diagnostic purposes. A zserp9 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

Zserp9 polypeptide fusions will generally contain not more than about 1500 amino acid residues, often not more than about 1200 residues, more often not more than about 1000 residues, and will in many cases be considerably smaller. For example, a zserp9 polypeptide of 423 residues (residues 3–425 of SEQ ID NO:2) can be fused to *E. coli* β-galactosidase (1,021 residues; see Casadaban et al., *J. Bacteriol.* 143:971–980, 1980) and a 10-residue spacer to yield a polypeptide of 1448 residues. In a second example, residues 1–425 of SEQ ID NO:2 are fused to maltose binding protein (approximately 370 residues), a 4-residue cleavage site, and a 6-residue polyhistidine tag. In a third example, residues 1–425 of SEQ ID NO:2 are fused at the C terminus to an IgG Fc fragment of 232 residues and at the amino terminus to a secretory peptide of 25 residues to yield a primary translation product of 682 residues and a processed polypeptide of 657 residues.

Linker peptides and affinity tags provide for additional functions, such as binding to substrates, antibodies, binding proteins, and the like, and facilitate purification, detection, and delivery of zserp9 proteins. Within certain embodiments of the invention, a zserp9 polypeptide is prepared as a fusion protein to facilitate purification, and the fusion is subsequently cleaved to release the zserp9 portion. In another example, a zserp9 polypeptide is expressed as a secreted protein comprising a carboxyl-terminal receptor transmembrane domain, permitting the zserp9 polypeptide to be displayed on the surface of a cell. To span the lipid bilayer of the cell membrane, a minimum of about 20 amino acids are required in the transmembrane domain; these should predominantly be hydrophobic amino acids. The zserp9 polypeptide can be separated from the transmembrane domain by a spacer polypeptide, and can be contained within an extended polypeptide comprising a carboxyl-terminal transmembrane domain-spacer polypeptide-zserp9-amino-terminal polypeptide. Many receptor transmembrane domains and polynucleotides encoding them are known in the art. The spacer polypeptide will generally be at least about 50 amino acid residues in length, up to 200–300 or more residues. The amino terminal polypeptide may be up to 300 or more residues in length.

Also disclosed herein are polynucleotide molecules, including DNA and RNA molecules, encoding zserp9 proteins. These polynucleotides include the sense strand; the anti-sense strand; and the DNA as double-stranded, having both the sense and anti-sense strand hydrogen bonded together. A representative DNA sequence encoding a human zserp9 protein is set forth in SEQ ID NO:1. DNA sequences encoding other zserp9 proteins can be readily generated by those of ordinary skill in the art based on the genetic code. Counterpart RNA sequences can be generated by substitution of U for T. Polynucleotides encoding zserp9 proteins and complementary polynucleotides are useful in the production of zserp9 proteins and for diagnostic and investigatory purposes.

Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zserp9 polypeptide of SEQ ID NO:2. Those skilled in the art will recognize that the degenerate sequence of SEQ ID NO:3 also provides all RNA sequences encoding SEQ ID NO:2 by substituting U for T. Thus, zserp9 polypeptide-encoding polynucleotides comprising nucleotide 1 to nucleotide 1275 of SEQ ID NO:3, polynucleotides comprising nucleotide 10 to nucleotide 1275 of SEQ ID NO:3, and their respective RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences shown in SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–1912, 1980; Haas et al. *Curr. Biol.* 6:315–324, 1996; Wain-Hobson et al., *Gene* 13:355–364, 1981; Grosjean and Fiers, *Gene* 18:199–209, 1982; Holm, *Nuc. Acids Res.* 14:3075–3087, 1986; and Ikemura, *J. Mol. Biol.* 158:573–597, 1982. "Preferential codon usage" is a term of art referring to the bias in codon usage within the genomes of certain species, whereby certain protein translation codons are more frequently used, thus favoring one or a few representatives of the possible codons encoding each amino acid (see Table 2). For example, the amino acid threonine (Thr) can be encoded by ACA, ACC, ACG, or ACT, but in mammalian cells ACC is the most commonly used codon. In other species, for example, insect cells, yeast, viruses or bacteria, different Thr codons may be preferred. Preferred codons for a particular species can be introduced into the polynucleotides of the present invention by a variety of methods known in the art. Introduction of preferred codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferred codons can be tested and optimized for expression in various host cell species, and tested for functionality as disclosed herein.

It is preferred that zserp9 polynucleotides hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, zserp9-encoding polynucleotides include DNA and RNA. Methods for preparing DNA and RNA are well known in the art. In general, RNA is isolated from a tissue or cell that produces large amounts of zserp9 RNA. Such tissues and cells are identified by conventional procedures, such as Northern blotting (Thomas, *Proc. Natl. Acad. Sci. USA* 77:5201, 1980) or PCR (Mullis, U.S. Pat. No. 4,683,202) and include fetal heart, cervix, melanoma, adipocyte, and testis. Total RNA can be prepared using guanidine-HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding zserp9 polypeptides are then identified and isolated by, for example, hybridization or PCR.

Clones encoding zserp9 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zserp9, receptor fragments, or other specific binding partners.

The polynucleotides of the present invention can also be synthesized using automated equipment ("gene machines"). The current method of choice is the phosphoramidite method. If chemically synthesized, double-stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA*, ASM Press, Washington, D.C., 1994; Itakura et al., *Annu. Rev. Biochem.* 53: 323–356, 1984; and Climie et al., *Proc. Natl. Acad. Sci. USA* 87:633–637, 1990.

The zserp9 polynucleotide sequences disclosed herein can be used to isolate counterpart polynucleotides from other species (orthologs). These orthologous polynucleotides can be used, inter alia, as diagnostic reagents, experimental standards, and to prepare the respective orthologous proteins for use in veterinary medicine. These other species include, but are not limited to, mammalian, avian, amphibian, reptile, fish, insect and other vertebrate and invertebrate species. Of particular interest are zserp9 polynucleotides and polypeptides from other mammalian species, including murine, porcine, ovine, bovine, canine, feline, equine, and other primate polypeptides. Orthologs of human zserp9 can be cloned using information and compositions provided by the present invention in combination with conventional cloning techniques. For example, a cDNA can be cloned using mRNA obtained from a tissue or cell type that expresses zserp9 as disclosed herein. A library is then prepared from mRNA of a positive tissue or cell line. A zserp9-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zserp9 sequence disclosed herein. Within an additional method, the cDNA library can be used to transform or transfect host cells, and expression of the cDNA of interest can be detected with an antibody to zserp9 polypeptide. Similar techniques can also be applied to the isolation of genomic clones.

Those skilled in the art will recognize that the sequence disclosed in SEQ ID NO:1 represents a single allele of human zserp9 and that natural variation, including allelic variation and alternative splicing, is expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs that retain the proteinase inhibiting activity of zserp9 are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The zserp9 polypeptides of the present invention, including full-length polypeptides, biologically active or immunogenic fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zserp9 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zserp9 polypeptide into the secretory pathway of a host cell, a secretory signal sequence (also known as a leader sequence, prepro sequence or pre sequence) is provided in the expression vector. The secretory signal sequence may be derived from another secreted protein (e.g., t-PA or *S. cerevisiae* alpha factor) or synthesized de novo. The secretory signal sequence is operably linked to the zserp9 DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al.,*J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, 10801 University Boulevard, Manassas, Va. Suitable promoters include those from metallothionein genes (U.S. Pat. Nos. 4,579,821 and 4,601,978), SV-40, cytomegalovirus (U.S. Pat. No. 4,956,288), and the adenovirus major late promoter. Expression vectors for use in mammalian cells include pZP-1 and pZP-9, which have been deposited with the American Type Culture Collection, 10801 University Boulevard, Manassas, Va. under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47–58, 1987. Insect cells can be infected with recombinant baculovirus vectors, which are commonly derived from *Autographa californica* multiple nuclear polyhedrosis virus (AcMNPV). DNA encoding the polypeptide of interest is inserted into the viral genome in place of the polyhedrin gene coding sequence by homologous recombination in cells infected with intact, wild-type AcMNPV and transfected with a transfer vector comprising the cloned gene operably linked to polyhedrin gene promoter, terminator, and flanking sequences. The resulting recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. For example, production of recombinant proteins in *Pichia methanolica* is disclosed in U.S. Pat. Nos. 5,716,808, 5,736, 383, 5,854,039, and 5,888,768. See also, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Prokaryotic host cells, including strains of the bacteria *Escherichia coli, Bacillus*, and other genera are also useful host cells within the present invention. Techniques for transforming these hosts and expressing foreign DNA sequences cloned therein are well known in the art (see, e.g., Sambrook et al., ibid.). When expressing a zserp9 polypeptide in bacteria such as *E. coli*, the polypeptide may be retained in the cytoplasm or may be directed to the periplasmic space by a bacterial secretion sequence. In the former case, the cells are lysed, and the zserp9 polypeptide is recovered from the lysate. If the polypeptide is present in the cytoplasm as insoluble granules, the cells are lysed, and the granules are recovered and denatured using, for example, guanidine isothiocyanate or urea. The denatured polypeptide can then be refolded by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors.

It is preferred to purify the proteins of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zserp9 proteins are purified by conventional protein purification methods, typically by a combination of chromatographic techniques. Polypeptides comprising a polyhistidine affinity tag (typically about 6 histidine residues) are purified by affinity chromatography on a nickel chelate resin. See, for example, Houchuli et al., *Bio/Technol.* 6: 1321–1325, 1988.

Using methods known in the art, zserp9 proteins can be produced glycosylated or non-glycosylated; PEGylated or non-PEGylated; and may or may not include an initial methionine amino acid residue. The actual structure of a recombinant protein will depend in part on the chosen host cell due to, for example, post-translational processing or proteolysis.

Within the present invention, zserp9 polypeptides, including variants and fragments of SEQ ID NO:2, can be tested for serine proteinase inhibitory activity using conventional assays. Briefly, substrate cleavage is conveniently assayed using a tetrapeptide that mimics the cleavage site of the natural substrate of the serine proteinase, and which is linked, via a peptide bond, to a carboxyl-terminal para-nitroanilide (pNA) group. The proteinase hydrolyzes the bond between the fourth amino acid residue and the pNA group, causing the pNA group to undergo a dramatic increase in absorbance at 405 nm. Such substrates will preferably contain an Arg residue at the $P_1$ position. Suitable substrates can be synthesized according to known methods or obtained from commercial suppliers. Assays of this type are well known in the art. See, for example, Lottenberg et al., *Thrombosis Research* 28:313–332, 1982; Cho et al., *Biochem.* 23:644–650, 1984; and Foster et al., *Biochem.* 26:7003-7011, 1987). The target proteinase is assayed in the absence of the zserp9 polypeptide and in the presence of increasing amounts of the zserp9 polypeptide. In a typical procedure, the inhibitory activity of a zserp9 polypeptide is measured by incubating the polypeptide with the proteinase, then adding an appropriate substrate, typically a chromogenic peptide substrate. See, for example, Norris et al. (*Biol. Chem. Hoppe-Seyler* 371:37–42, 1990). For example, various concentrations of the polypeptide are incubated in the presence of thrombin in a low-salt buffer at pH 7.4, 25° C. After 30 minutes, the residual enzymatic activity is measured by the addition of a chromogenic substrate (e.g., S-2238 (H-D-Phe-Pip-Arg-pNA.2HCl), S-2288 (H-D-Ile-Pro-Arg-pNA.2HCl), or S-2765 (Z-D-Arg-Gly-Arg-pNA.2HCl), available from DiaPharma Group, West Chester, Ohio) and a 30-minute incubation. Inhibition of enzyme activity is indicated by a decrease in absorbance at 405 nm or fluorescence Em at 460 nm. From the results, the apparent inhibition constant $K_i$ is calculated. The inhibition of coagulation factors (e.g., factor VIIa, factor Xa) can be measured using chromogenic substrates or in conventional coagulation assays (e.g., clotting time of normal human plasma; Dennis et al., *J. Biol. Chem.* 270:25411–25417, 1995).

Effects of zserp9 polypeptides on inflammatory processes can be tested using assays that are known in the art. Exemplary assays include mitogenesis assays in which IL-1 responsive cells (e.g., D10.N4.M cells) are incubated in the presence of IL-1 with and without zserp9 polypeptide for 72 hours at 37° C. in a 5% $CO_2$ atmosphere. IL-2 (and optionally IL-4) is added to the culture medium to enhance sensitivity and specificity of the assay. [$^3$H]thymidine is then added, and incubation is continued for six hours. The amount of label incorporated is indicative of relative pro-inflammatory activity. See, Hopkins and Humphreys, *J. Immunol. Methods* 120:271–276, 1989; Greenfeder et al., *J. Biol. Chem.* 270:22460–22466, 1995. IL-1 stimulation of cell proliferation can also be measured using thymocytes cultured in IL-1 in combination with phytohemagglutinin. Proliferation is detected as [$^3$H]thymidine incorporation or through the use of a colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, 1983). Briefly, a solution of MTT is added to 100 μl of assay cells, and the cells are incubated at 37° C. After 4 hours, 200 μl of 0.04 N HCl in isopropanol is added, the solution is mixed, and the absorbance of the sample is measured at 570 nm.

Zserp9 proteins can be tested in animal models of disease, particularly tumor models, models of inflammation, models of fibrinolysis, models of imbalance of hemostasis, and models of autoimmune disease. Suitable models are known in the art. For example, inhibition of tumor metastasis can be assessed in mice into which cancerous cells or tumor tissue have been introduced by implantation or injection (e.g., Brown, *Advan. Enzyme Regul.* 35:293–301, 1995; Conway et al., *Clin. Exp. Metastasis* 14:115–124, 1996). Effects on fibrinolysis can be measured in a rat model wherein the enzyme batroxobin and radiolabeled fibrinogen are administered to test animals. Inhibition of fibrinogen activation by a test compound is seen as a reduction in the circulating level of the label as compared to animals not receiving the test compound. See, Lenfors and Gustafsson, *Semin. Thromb. Hemost.* 22:335–342, 1996. Zserp9 proteins can be delivered to test animals by injection or infusion, or can be produced in vivo by way of, for example, viral or naked DNA delivery systems or transgenic expression. Many models of inflammation are known in the art. Animal models of psoriasis include the analysis of histological alterations in adult mouse tail epidermis (Hofbauer et al, *Brit. J. Dermatol.* 118:85–89, 1988; Bladon et al., *Arch Dermatol. Res.* 277:121–125, 1985). In this model, anti-psoriatic activity is indicated by the induction of a granular layer and orthokeratosis in areas of scale between the hinges of the tail epidermis. Typically, a topical ointment is applied daily for seven consecutive days, then the animal is sacrificed, and tail skin is examined histologically. An additional model is provided by grafting psoriatic human skin to congenitally athymic (nude) mice (Krueger et al., *J. Invest. Dermatol.* 64:307–312, 1975). Such grafts have been shown to retain the characteristic histology for up to eleven weeks. As in the mouse tail model, the test composition is applied to the skin at predetermined intervals for a period of one to several weeks, at which time the animals are sacrificed and the skin grafts examined histologically. A third model has been disclosed by Fretland et al. (*Inflammation* 14:727–739, 1990). Briefly, inflammation is induced in guinea pig epidermis by topically applying phorbol ester (phorbol-12-myristate-13-acetate; PMA), typically at ca. 2 mg/ml in acetone, or the calcium ionophore A23187, typically at 200 nmol in 0.1 ml DMSO, to one ear and vehicle to the contralateral ear. Test compounds are applied concurrently with the inflammatory agent. Histological analysis is performed at 96 hours after induction of inflammation. This model duplicates many symptoms of human psoriasis, including edema, inflammatory cell diapedesis and infiltration, high $LTB_4$ levels, and epidermal proliferation.

Cerebral ischemia can be studied in a rat model as disclosed by Relton et al., *Exp. Neurol.* 138:206–213, 1996 and Loddick et al., *Biochem. Biophys. Res. Comm.* 234:211–215, 1997. Zserp9 proteins can be delivered to test animals by injection or infusion, or can be produced in vivo by way of, for example, viral or naked DNA delivery systems or transgenic expression.

Exemplary viral delivery systems include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–189, 1994; and Douglas and Curiel, *Science & Medicine* 4:44–53, 1997). The adenovirus system offers several advantages: adenovirus can (i) accommodate relatively large DNA inserts; (ii) be grown to high titer; (iii) infect a broad range of mammalian cell types; and (iv) be used with a large number of available vectors containing different promoters. Also, because adenoviruses are stable in the bloodstream, they can be administered by intravenous injection. By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

In another method, the vector can be introduced by "lipofection" in vivo using liposomes. Synthetic cationic lipids can be used to prepare liposomes for in vivo transfection (Felgner et al., *Proc. Natl. Acad. Sci. USA* 84:7413–7417, 1987; Mackey et al., *Proc. Natl. Acad. Sci. USA* 85:8027–8031, 1988). The use of lipofection to introduce exogenous genes into specific organs in vivo has certain practical advantages, including molecular targeting of liposomes to specific cells. Directing transfection to particular cell types is particularly advantageous in tissues with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Transgenic mice, engineered to express a zserp9 gene, and mice that exhibit a complete absence of zserp9 gene function, referred to as "knockout mice" (Snouwaert et al., *Science* 257:1083, 1992), can also be generated (Lowell et al., *Nature* 366:740–742, 1993). These mice are employed to study the zserp9 gene and the encoded protein in an in vivo system. Transgenic mice are particularly useful for investigating the role of zserp9 proteins in early development because they allow the identification of developmental abnormalities or blocks resulting from the over- or under-expression of a specific factor.

Zserp9 polypeptides are contemplated for use in the treatment or prevention of conditions associated with excessive proteinase activity. Such conditions include, but are not limited to, inflammatory disorders, blood coagulation disorders, thrombotic disorders, tumor metastases, and autoimmune diseases. The zserp9 polypeptides of the present invention may be combined with other therapeutic agents to augment the activity (e.g., antithrombotic or anti-coagulant activity) of such agents.

Zserp9 polypeptides may be used to modulate inflammation and related processes. Of particular interest is the reduction of inflammation. Thus, zserp9 polypeptides may be used to treat or prevent chronic inflammatory diseases such as arthritis (including rheumatoid arthritis, osteoarthritis, and Lyme arthritis) and psoriasis; to reduce tissue damage after ischemia; and to treat septic shock, graft-versus-host disease, and leukemia. Other inflammatory conditions that may be responsive to treatment with zserp9 polypeptides include inflammatory bowel disease (including Crohn's disease and ulcerative colitis) (reviewed by Hendel et al., *Exp. Opin. Invest. Drugs* 5:843–850, 1996; see also, Cominelli et al., *Gastroenterology* 103:65–71, 1992), insulin-dependent diabetes mellitus (reviewed by Mandrup-Poulsen et al., *Cytokine* 5:185–191, 1993; see also, Dayer-Metroz et al., *Eur. J. Clin. Inv.* 22:A50, 1992), acute pancreatitis (Norman et al., *Ann. Surg.* 221:625–634, 1995), glomerulonephritis (Lan et al., *Kidney Int.* 47:1303–1309, 1995), and cerebral ischemia (Relton et al., *Exp. Neurology* 138:206–213, 1996; Loddick et al., *Biochem. Biophys. Res. Comm.* 234:211–215, 1997).

Zserp9 proteins may be useful in the treatment of conditions arising from an imbalance in hemostasis, including acquired coagulopathies, primary fibrinolysis and fibrinolysis due to cirrhosis, and complications from high-dose thrombolytic therapy. Acquired coagulopathies can result from liver disease, uremia, acute disseminated intravascular coagulation, post-cardiopulmonary bypass, massive transfusion, or Warfarin overdose (Humphries, *Transfusion Medicine* 1:1181–1201, 1994). A deficiency or dysfunction in any of the procoagulant mechanisms predisposes the patient to either spontaneous hemorrhage or excess blood loss associated with trauma or surgery. Acquired coagulopathies usually involve a combination of deficiencies, such as deficiencies of a plurality of coagulation factors, and/or platelet dysfunction. In addition, patients with liver disease commonly experience increased fibrinolysis due to an inability to maintain normal levels of $\alpha_2$-antiplasmin and/or decreased hepatic clearance of plasminogen activators (Shuman, *Hemorrhagic Disorders*, in Bennet and Plum, eds. *Cecil Textbook of Medicine*, 20th ed., W. B. Saunders Co., 1996). Primary fibrinolysis results from a massive release of plasminogen activator. Conditions associated with primary fibrinolysis include carcinoma of the prostate, acute promyelocytic leukemia, hemangiomas, and sustained release of plasminogen activator by endothelial cells due to injection of venoms. The condition becomes critical when enough plasmin is activated to deplete the circulating level of $\alpha_2$-antiplasmin (Shuman, ibid.). Data suggest that plasmin on endothelial cells may be related to the pathophysiology of bleeding or rethrombosis observed in patients undergoing high-dose thrombolytic therapy for thrombosis. Plasmin may cause further damage to the thrombogenic surface of blood vessels after thrombolysis, which may result in rethrombosis (Okajima, *J. Lab. Clin. Med.* 126:1377–1384, 1995).

Additional antithrombotic uses of zserp9 proteins include treatment or prevention of deep vein thrombosis, pulmonary embolism, and post-surgical thrombosis.

Zserp9 proteins may also be used within methods for inhibiting blood coagulation in mammals, such as in the treatment of disseminated intravascular coagulation. Zserp9 proteins may thus be used in place of known anticoagulants such as heparin, coumarin, and anti-thrombin III. Such methods will generally include administration of the protein in an amount sufficient to produce a clinically significant inhibition of blood coagulation. Such amounts will vary with the nature of the condition to be treated, but can be predicted on the basis of known assays and experimental animal models, and will in general be within the ranges disclosed below.

Doses of zserp9 polypeptides will vary according to the severity of the condition being treated and may range from approximately 10 $\mu$g/kg to 10 mg/kg body weight, preferably 100 $\mu$g/kg to 5 mg/kg, more preferably 100 $\mu$g/kg to 1 mg/kg. Life-threatening conditions will usually be treated with large doses. The polypeptides are formulated in a pharmaceutically acceptable carrier or vehicle. It is preferred to prepare them in a form suitable for injection or infusion, such as by dilution with with sterile water, an isotonic saline or glucose solution, or similar vehicle. In the alternative, the protein may be packaged as a lyophilized powder, optionally in combination with a pre-measured diluent, and resuspended immediately prior to use. Pharmaceutical compositions may further include one or more excipients, preservatives, solubilizers, buffering agents, albumin to prevent protein loss on vial surfaces, etc. Formulation methods are within the level of ordinary skill in the art. See, *Remington: The Science and Practice of Pharmacy*, Gennaro, ed., Mack Publishing Co., Easton, Pa., 19th ed., 1995.

Gene therapy provides an alternative therapeutic approach for delivery of zserp9 proteins. If a mammal has a mutated or absent zserp9 gene, a polynucleotide encoding a zserp9 protein can be introduced into the cells of the mammal. In one embodiment, a gene encoding a zserp9 protein is introduced in vivo in a viral vector. Such vectors include an attenuated or defective DNA virus, such as herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, without limitation, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

Within another embodiment, a zserp9 polynucleotide can be introduced in a retroviral vector, as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., J. Virol. 62:1120, 1988; Temin et al., U.S. Pat. No. 5,124, 263; Dougherty et al., WIPO Publication No. WO 95/07358; and Kuo et al., Blood 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988).

Within a further embodiment, a zserp9-encoding vector is introduced into the cells as a naked DNA plasmid as generally disclosed above.

Zserp9 polypeptides can be used to prepare antibodies that specifically bind to zserp9 polypeptides. As used herein, the term "antibodies" includes polyclonal antibodies, monoclonal antibodies, antigen-binding fragments thereof such as $F(ab')_2$ and Fab fragments, single chain antibodies, and the like, including genetically engineered antibodies. Non-human antibodies can be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Alternative techniques for generating or selecting antibodies useful herein include in vitro exposure of lymphocytes to a zserp9 polypeptide, and selection of antibody display libraries in phage or similar vectors (for instance, through use of immobilized or labeled zserp9 polypeptide). Antibodies are defined to be specifically binding if they bind to a zserp9 polypeptide with an affinity at least 10-fold greater than the binding affinity to a control (non-zserp9) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art. See for example, Hurrell, J. G. R., Ed., *Monoclonal Hybridoma Antibodies: Techniques and Applications*, CRC Press, Inc., Boca Raton, Fla., 1982. As would be evident to one of ordinary skill in the art, polyclonal antibodies can be generated from a variety of warm-blooded animals such as horses, cows, goats, sheep, dogs, chickens, rabbits, mice, and rats. The immunogenicity of a zserp9 protein may be increased through the use of an adjuvant such as alum (aluminum hydroxide) or Freund's complete or incomplete adjuvant. Polypeptides useful for immunization also include fusion polypeptides, such as fusions of a zserp9 protein or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Immunogenic zserp9 polypeptides will generally comprise at least 15 contiguous amino acid residues of SEQ ID NO:2 and will comprise an epitope-bearing portion of a polypeptide as shown in SEQ ID NO:2. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979). Anti-peptide antibodies are not conformation-dependent and can be used to detect proteins in fragmented or otherwise altered forms (Niman et al., *Proc. Natl. Acad. Sci. USA* 82:7924–7928, 1985), such as might occur in body fluids or cell culture media. Antibodies to short peptides may also recognize proteins in native conformation and will thus be useful for monitoring protein expression and protein isolation, and in detecting zserp9 proteins in solution, such as by ELISA or in immunoprecipitation studies. It is preferred to use polypeptides that are hydrophilic or comprise a hydrophilic region. Preferred such regions of SEQ ID NO:2 include residues 21–26, 45–50, 65–70, 105–110, 138–143, 169–174, 171–176, 185–190, 223–228, 281–286, 282–287, 306–311, and 307–312 of SEQ ID NO:2. Longer immunogenic polypeptides include those comprising residues 64–110, 169–190, or 281–312 of SEQ ID NO:2. Such longer immunogenic polypeptides include those comprising at least 30, at least 40, at least 50, at least 60, at least 75, at least 100, at least 150, at least 200, at least 250, at least 300, at least 350, or at least 400 contiguous amino acid residues of SEQ ID NO:2.

A variety of assays known to those skilled in the art can be utilized to detect antibodies that specifically bind to a zserp9 polypeptide. Exemplary assays are described in detail in *Antibodies: A Laboratory Manual*, Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zserp9 may be used for affinity purification of zserp9 polypeptides; within diagnostic assays for determining circulating levels of zserp9 polypeptides; for detecting or quantitating soluble zserp9 polypeptide as a marker of underlying pathology or disease; for immunolocalization within whole animals or tissue sections, including immunodiagnostic applications; for immunohistochemistry; for screening expression libraries; and for other uses that will be evident to those skilled in the art. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles, and the like; indirect tags or labels may feature use of biotin-avidin or other complement/anti-complement pairs as intermediates.

Production of zserp9 in patients or experimental animals can be suppressed using inhibitory polynucleotides, which can be used to inhibit zserp9 gene transcription or translation. Polynucleotides that are complementary to a segment of a zserp9-encoding polynucleotide (e.g., a polynucleotide as set forth in SEQ ID NO:1) are designed to bind to zserp9-encoding mRNA and to inhibit translation of such mRNA. Such antisense polynucleotides can be targetted to specific tissues using a gene therapy approach with specific vectors and/or promoters, such as viral delivery systems. Ribozymes can also be used as zserp9 antagonists. Ribozymes are RNA molecules that contains a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme. In another approach, expression vectors can be constructed in which a regulatory element directs the production of RNA transcripts capable of promoting RNase P-mediated cleavage of mRNA molecules that encode a zserp9 polypeptide. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., *Science* 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten-to fifteen-nucleotide sequence complementary to zserp9 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

The present invention also provides reagents for use in diagnostic applications. For example, the zserp9 gene, a probe comprising zserp9 DNA or RNA, or a subsequence thereof can be used to determine the presence of mutations at or near the zserp9 locus at human chromosome 18q21.31. This region of human chromosome 18 has been linked to erythropoietic protoporphyra (Inazawa et al., *Cytogenet. Cell Genet*. 58:2014, 1991; Brenner et al., *Am. J. Hum. Genet*. 50:1203–1210, 1992), B-cell chronic lymphocytic leukemia, and follicular lymphomas (Rimokh et al., *Blood* 81:136–142, 1993). Detectable chromosomal aberrations at the zserp9 gene locus include, but are not limited to, aneuploidy, gene copy number changes, insertions, deletions, restriction site changes, translocations, and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targetted for analysis. For gross analysis of genes, a polynucleotide probe may comprise an entire exon or more. Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–265, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–38, 1991).

The polypeptides, nucleic acid and/or antibodies of the present invention may be used in diagnosis or treatment of disorders associated with cell loss or abnormal cell proliferation (including cancer). As shown below, zserp9 is expressed in melanoma. Labeled anti-zserp9 antibodies may be used for imaging tumors or other sites of abnormal cell proliferation. Zserp9 polypeptides may be used as standards in assays to detect the presence of zserp9 polypeptides in biological samples, including tissue samples and biological fluids (e.g., serum, lymph, urine).

Zserp9 polypeptides can be used in research and industry to reduce proteolysis during protein production (including production using cultured cells), purification, and processing. See, in general, Deutscher, *Methods Enzymol*. 182:83–89, 1990. Because of their widespread distribution, serine proteinases often contribute to the degradation of proteins during purification. Proteolysis can occur at all stages of protein purification, but is most often encountered in the early stages, when more contaminating proteins are present. Of particular interest is the inhibition of cellular proteases, which can be release during cell lysis. Zserp9 polypeptides can be used alone or in combination with one or more other proteinase inhibitors to provide a "cocktail" with a broad spectrum of activity. The proteins can also be used in the laboratory as a tissue culture additive to prevent cell detachment. In general, zserp9 polypeptides will be used at a concentration of about 10 ng/ml–100 µg/ml, typically about 1 µg/ml.

Zserp9 polypeptides can be used to remove serine proteinases from mixtures. Within one such application, a zserp9 polypeptide is coupled to a solid support using conventional coupling chemistries. Suitable supports in this regard include glass beads, silica-based resins, cellulosic resins, agarose beads, cross-linked agarose beads, polystyrene beads, cross-linked polyacrylamide resins, and the like that are insoluble under the conditions in which they are to be used. These supports can be modified with reactive groups that allow attachment of polypeptides through, for example, amino groups, carboxyl groups, sulfhydryl groups, hydroxyl groups, and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. In a typical procedure, the resin-polypeptide complex is packed into a column, and an aqueous mixture containing a proteinase is applied to the column. In general, the mixture is buffered at a pH compatible with the activity optimum of the proteinase to maximize binding of the proteinase to the zserp9 polypeptide. The proteinase is allowed to bind to the immobilized polypeptide, and the other components of the mixture pass through the column. The column is washed at the pH of the loading buffer to remove additional unbound mixture components. The bound proteinase can be eluted from the column with buffers that disrupt protein-protein interactions, such as chaotropic salts (e.g., KSCN) or high or low pH buffers. Such procedures can be adapted by those of ordinary skill in the art for purification of proteinases or for removal of proteinases from process streams.

Polynucleotides and polypeptides of the present invention will additionally find use as educational tools within laboratory practicum kits for courses related to genetics, molecular biology, protein chemistry, and antibody production and analysis. Due to their unique polynucleotide and polypeptide sequences, zserp9 molecules can be used as standards or as "unknowns" for testing purposes. For example, zserp9 polynucleotides can be used as aids in teaching a student how to prepare expression constructs for bacterial, viral, and/or mammalian expression, including fusion constructs, wherein a zserp9 gene or cDNA is to be expressed; for determining the restriction endonuclease cleavage sites of the polynucleotides; determining mRNA and DNA localization of zserp9 polynucleotides in tissues (e.g., by Northern blotting, Southern blotting, or polymerase chain reaction); and for identifying related polynucleotides and polypeptides by nucleic acid hybridization. Zserp9 polypeptides can be used educationally as aids to teach preparation of antibodies; identification of proteins by Western blotting; protein purification; determination of the weight of expressed zserp9 polypeptides as a ratio to total protein expressed; identification of peptide cleavage sites; coupling of amino and carboxyl terminal tags; amino acid sequence analysis, as well as, but not limited to, monitoring biological activities of both the native and tagged protein (e.g., receptor binding, signal transduction, proliferation, and differentiation) in vitro and in vivo. Zserp9 polypeptides can also be used to teach analytical skills such as mass spectrometry, circular dichroism to determine conformation, x-ray crystallography to determine the three-dimensional structure in atomic detail, nuclear magnetic resonance spectroscopy to reveal the structure of proteins in solution, and the like. For example, a kit containing a zserp9 polypeptide can be given to a student to analyze. Since the amino acid sequence would be known by the instructor, the polypeptide can be given to the student as a test to determine the skills or develop the skills of the student, and the instructor would then know whether or not the student has correctly analyzed the polypeptide. Since every polypeptide is unique, the educational utility of zserp9 would be unique unto itself.

The invention is further illustrated by the following, non-limiting example.

EXAMPLE

A variety of cDNAs, cDNA libraries, and arrayed cDNA libraries (libraries broken down into small pools) from the tissues listed in Table 3 were screened for the presence of zserp9 sequence by PCR using oligonucleotide primers ZC38,167 (SEQ ID NO:5) and ZC38,168 (SEQ ID NO:6). Reaction mixtures were incubated at 94° C. for two minutes; followed by 35 cycles of 94° C. for 15 seconds, 62° C. for 30 seconds, and 72° C. for 30 seconds; then 72° C. for seven minutes; then held at 4° C. Positive samples produced a PCR product 356 bp in length. Results are shown in Table 3.

TABLE 3

| Template | Result | Template | Result |
|---|---|---|---|
| Adrenal Gland | − | Bladder | − |
| Bone Marrow | − | Brain | − |
| Cervix | + | Colon | − |
| Fetal Brain | − | Fetal Heart | − |
| Fetal Kidney | − | Fetal Liver | − |
| Fetal Lung | − | Fetal Muscle | − |
| Fetal Skin | − | Heart | − |
| K562 (keratinocyte) | − | Kidney | − |
| Liver | − | Lung | − |
| Lymph Node | − | Mammary Gland | − |
| Melanoma | + | Ovary | − |
| Pancreas | − | Pituitary | − |
| Placenta | − | Prostate | − |
| Rectum | − | Salivary Gland | − |
| Skeletal Muscle | − | Small Intestine | − |
| Spinal Cord | − | Spleen | − |
| Stomach | − | Testis | − |
| Thymus | − | Thyroid | − |
| Trachea | − | Uterus | − |
| Adipocyte Library | + | Brain Library | + |
| Fetal Brain Library | + | Fetal Liver Library | + |
| Islet Library | +/− | Kidney Library | + |
| Prostate 0.5–1.6 kb | − | Prostate >1.6 kb | − |
| Prostate Smooth Muscle Cell | − | RPMI 1788 (B-cell; ATCC # CCL-156) | +/− |
| Spinal Cord | − | Thyroid Library | − |
| WI-38 (diploid embryonic lung) Library | − | Arrayed Bone | − |
| Arrayed Fetal Brain | − | Arrayed Heart | − |
| Arrayed Pituitary | − | Arrayed Placenta | − |
| Arrayed Placenta | − | Arrayed Testis 1K | + |
| Arrayed Testis 10K | + | Tumor Esophagus | − |
| Tumor Liver | − | Tumor Lung | − |
| Tumor Ovary | − | Tumor Rectum | − |
| Tumor Stomach | − | Tumor Uterus | − |
| Genomic (positive control) | +/− | Bone Marrow | − |
| CD3+ Library | − | HaCAT (keratinocyte) Library | +/− |
| HPV (prostate epithelia; ATCC # CRL-2221) | +/− | HPVS (ATCC # CRL-2221) (prostate epitelilia, selected) Library | +/− |
| MG63 (osteosarcoma) Library | − | Testis Library | + |

From the foregoing, it will be appreciated that, although specific embodiments of the invention have been described

What is claimed is:

1. An isolated polypepide consisting of residues 3–425 of SEQ ID NO:2, residues 2–425 of SEQ ID NO:2, or residues 1–425 of SEQ ID NO:2.

2. The polypeptide of claim 1, wherein said polypeptide consists of residues 3–425 of SEQ ID NO:2.

3. The polypeptide of claim 1, wherein said polypeptide consists of residues 2–425 of SEQ ID NO:2.

4. The polypeptide of claim 1, wherein said polypeptide consists of residues 1–425 of SEQ ID NO:2.

* * * * *

SEQUENCE LISTING

```
<160> NUMBER OF SEQ ID NOS: 6

<210> SEQ ID NO 1
<211> LENGTH: 3603
<212> TYPE: DNA
<213> ORGANISM: Homo sapiens
<220> FEATURE:
<221> NAME/KEY: CDS
<222> LOCATION: (69)...(1346)

<400> SEQUENCE: 1
```

| | | | | | | | | | | | | | | | |
|---|---|---|---|---|---|---|---|---|---|---|---|---|---|---|---|
| gggggaagct | tacctgacca | gcagttagca | gcaactctga | gggcaagaag | atcgttataa | | | | | | | | | | 60 |

| gttttaca | atg | gac | tct | ctt | gtt | aca | gca | aac | acc | aaa | ttt | tgc | ttt | gat | 110 |
|---|---|---|---|---|---|---|---|---|---|---|---|---|---|---|---|
| | Met | Asp | Ser | Leu | Val | Thr | Ala | Asn | Thr | Lys | Phe | Cys | Phe | Asp | |
| | 1 | | | | 5 | | | | | 10 | | | | | |

| ctt | ttt | caa | gag | ata | ggc | aaa | gat | gat | cgt | cat | aaa | aac | ata | ttt | ttc | 158 |
|---|---|---|---|---|---|---|---|---|---|---|---|---|---|---|---|---|
| Leu | Phe | Gln | Glu | Ile | Gly | Lys | Asp | Asp | Arg | His | Lys | Asn | Ile | Phe | Phe | |
| 15 | | | | | 20 | | | | | 25 | | | | | 30 | |

| tct | ccc | ctg | agc | ctc | tca | gct | gcc | ctt | ggt | atg | gta | cgc | ttg | ggt | gct | 206 |
|---|---|---|---|---|---|---|---|---|---|---|---|---|---|---|---|---|
| Ser | Pro | Leu | Ser | Leu | Ser | Ala | Ala | Leu | Gly | Met | Val | Arg | Leu | Gly | Ala | |
| | | | | 35 | | | | | 40 | | | | | 45 | | |

| aga | agt | gac | agt | gca | cat | cag | att | gat | gag | gta | cta | cac | ttc | aac | gaa | 254 |
|---|---|---|---|---|---|---|---|---|---|---|---|---|---|---|---|---|
| Arg | Ser | Asp | Ser | Ala | His | Gln | Ile | Asp | Glu | Val | Leu | His | Phe | Asn | Glu | |
| | | 50 | | | | | 55 | | | | | 60 | | | | |

| ttt | tcc | cag | aat | gaa | agc | aaa | gaa | cct | gac | cct | tgt | ctg | aaa | agc | aac | 302 |
|---|---|---|---|---|---|---|---|---|---|---|---|---|---|---|---|---|
| Phe | Ser | Gln | Asn | Glu | Ser | Lys | Glu | Pro | Asp | Pro | Cys | Leu | Lys | Ser | Asn | |
| | | | 65 | | | | | 70 | | | | | 75 | | | |

| aaa | caa | aaa | gtg | ctg | gct | gac | agc | tct | ctg | gag | ggg | cag | aaa | aaa | acg | 350 |
|---|---|---|---|---|---|---|---|---|---|---|---|---|---|---|---|---|
| Lys | Gln | Lys | Val | Leu | Ala | Asp | Ser | Ser | Leu | Glu | Gly | Gln | Lys | Lys | Thr | |
| | 80 | | | | | 85 | | | | | 90 | | | | | |

| aca | gag | cct | ctg | gat | cag | cag | gct | ggg | tcc | tta | aac | aat | gag | agc | gga | 398 |
|---|---|---|---|---|---|---|---|---|---|---|---|---|---|---|---|---|
| Thr | Glu | Pro | Leu | Asp | Gln | Gln | Ala | Gly | Ser | Leu | Asn | Asn | Glu | Ser | Gly | |
| 95 | | | | | 100 | | | | | 105 | | | | | 110 | |

| ctg | gtc | agc | tgc | tac | ttt | ggg | cag | ctt | ctc | tcc | aaa | tta | gac | agg | atc | 446 |
|---|---|---|---|---|---|---|---|---|---|---|---|---|---|---|---|---|
| Leu | Val | Ser | Cys | Tyr | Phe | Gly | Gln | Leu | Leu | Ser | Lys | Leu | Asp | Arg | Ile | |
| | | | | 115 | | | | | 120 | | | | | 125 | | |

| aag | act | gat | tac | aca | ctg | agt | att | gcc | aac | agg | ctt | tat | gga | gag | cag | 494 |
|---|---|---|---|---|---|---|---|---|---|---|---|---|---|---|---|---|
| Lys | Thr | Asp | Tyr | Thr | Leu | Ser | Ile | Ala | Asn | Arg | Leu | Tyr | Gly | Glu | Gln | |
| | | | | 130 | | | | | 135 | | | | | 140 | | |

| gaa | ttc | cca | atc | tgt | cag | gaa | tac | ttg | gat | ggt | gtg | att | caa | ttt | tac | 542 |
|---|---|---|---|---|---|---|---|---|---|---|---|---|---|---|---|---|
| Glu | Phe | Pro | Ile | Cys | Gln | Glu | Tyr | Leu | Asp | Gly | Val | Ile | Gln | Phe | Tyr | |
| | | | 145 | | | | | 150 | | | | | 155 | | | |

| cac | acg | acg | att | gaa | agt | gtt | gat | ttc | caa | aaa | aac | cct | gaa | aaa | tcc | 590 |
|---|---|---|---|---|---|---|---|---|---|---|---|---|---|---|---|---|
| His | Thr | Thr | Ile | Glu | Ser | Val | Asp | Phe | Gln | Lys | Asn | Pro | Glu | Lys | Ser | |
| | | 160 | | | | | 165 | | | | | 170 | | | | |

| aga | caa | gag | att | aac | ttc | tgg | gtt | gaa | tgt | caa | tcc | caa | ggt | aaa | atc | 638 |
|---|---|---|---|---|---|---|---|---|---|---|---|---|---|---|---|---|
| Arg | Gln | Glu | Ile | Asn | Phe | Trp | Val | Glu | Cys | Gln | Ser | Gln | Gly | Lys | Ile | |
| 175 | | | | | 180 | | | | | 185 | | | | | 190 | |

| aag | gaa | ctc | ttc | agc | aag | gac | gct | att | aat | gct | gag | act | gtg | ctg | gta | 686 |
|---|---|---|---|---|---|---|---|---|---|---|---|---|---|---|---|---|
| Lys | Glu | Leu | Phe | Ser | Lys | Asp | Ala | Ile | Asn | Ala | Glu | Thr | Val | Leu | Val | |
| | | | | 195 | | | | | 200 | | | | | 205 | | |

| ctg | gtg | aat | gct | gtt | tac | ttc | aag | gcc | aaa | tgg | gaa | aca | tac | ttt | gac | 734 |
|---|---|---|---|---|---|---|---|---|---|---|---|---|---|---|---|---|
| Leu | Val | Asn | Ala | Val | Tyr | Phe | Lys | Ala | Lys | Trp | Glu | Thr | Tyr | Phe | Asp | |
| | | | 210 | | | | | 215 | | | | | 220 | | | |

| cat | gaa | aac | acg | gtg | gat | gca | cct | ttc | tgt | cta | aat | gcg | aat | gaa | aac | 782 |
|---|---|---|---|---|---|---|---|---|---|---|---|---|---|---|---|---|
| His | Glu | Asn | Thr | Val | Asp | Ala | Pro | Phe | Cys | Leu | Asn | Ala | Asn | Glu | Asn | |

-continued

```
                      225                     230                         235
aag agt gtg aag atg atg acg caa aaa ggc ctc tac aga att ggc ttc           830
Lys Ser Val Lys Met Met Thr Gln Lys Gly Leu Tyr Arg Ile Gly Phe
    240                     245                     250 ata gag gag gtg aag gca cag atc ctg gaa atg agg tac acc aag ggg           878
Ile Glu Glu Val Lys Ala Gln Ile Leu Glu Met Arg Tyr Thr Lys Gly
255                     260                     265                 270 aag ctc agc atg ttc gtg ctg ctg cca tct cac tct aaa gat aac ctg           926
Lys Leu Ser Met Phe Val Leu Leu Pro Ser His Ser Lys Asp Asn Leu
                275                     280                     285 aag ggt ctg gaa gag ctt gaa agg aaa atc acc cat gaa aaa atg gtg           974
Lys Gly Leu Glu Glu Leu Glu Arg Lys Ile Thr His Glu Lys Met Val
            290                     295                     300 gcc tgg agc agc tca gaa aac atg tca gaa gaa tcg gtg gtc ctg tcc          1022
Ala Trp Ser Ser Ser Glu Asn Met Ser Glu Glu Ser Val Val Leu Ser
        305                     310                     315 ttc ccc cgg ttc acc ctg gaa gac agc tat gat ctc aat tcc att tta          1070
Phe Pro Arg Phe Thr Leu Glu Asp Ser Tyr Asp Leu Asn Ser Ile Leu
    320                     325                     330 caa gac atg ggc att acg gat atc ttt gat gaa acg agg gct gat ctt          1118
Gln Asp Met Gly Ile Thr Asp Ile Phe Asp Glu Thr Arg Ala Asp Leu
335                     340                     345                 350 act gga atc tct cca agt ccc aat ttg tac ttg tca aaa att atc cac          1166
Thr Gly Ile Ser Pro Ser Pro Asn Leu Tyr Leu Ser Lys Ile Ile His
                355                     360                     365 aaa acc ttt gtg gag gtg gat gaa aac ggt acc cag gca gct gca gcc          1214
Lys Thr Phe Val Glu Val Asp Glu Asn Gly Thr Gln Ala Ala Ala Ala
            370                     375                     380 act ggg gct gtt gtc tcg gaa agg tca cta cga tct tgg gtg gag ttt          1262
Thr Gly Ala Val Val Ser Glu Arg Ser Leu Arg Ser Trp Val Glu Phe
        385                     390                     395 aat gcc aac cac cct ttt ctc ttt ttc att aga cac aac aaa acc caa          1310
Asn Ala Asn His Pro Phe Leu Phe Phe Ile Arg His Asn Lys Thr Gln
    400                     405                     410 acc att ctc ttt tat ggc agg gtc tgc tct cct taa aagggagca                1356
Thr Ile Leu Phe Tyr Gly Arg Val Cys Ser Pro  *
415                     420                     425 gtgtctagta ctttggagct ggaggaaaat atcaatacaa tcttcccctg cataagatg         1416
ggcatttgag tttttggtaa tatctaaagc atctccttca tcctccagcc atcggcttgt        1476
gcttatcttg atctttctgt caccctgtag cttattttca tctgagtctg ttagtattga        1536
agggctgttg ttctctaccc taaactttca agcatataaa ttcaccctct gtgacctgaa        1596
ggtcaacaca attcagaaca gtacctacct cctttgaag gaatcctaaa agttcaggtc         1656
attagaccat ttctaagaga tggcaaactc agaagccact ttaacatggg cagcaagaga        1716
acatgtttga ctggaacgtg tttggaaact cagctctgtt tctggggtag tttgaccgga        1776
acgtgtttgg aaactcagct ctgtttctgg atagttatg attgtggtca tcactgggcg         1836
agatgccctg tttcttcctt tgacagctac tgcatggaag atgtcctgtg aggtctttc         1896
acctaggaca aggcagggct tggcgtatt taagtgatag ctcaaagatg tgtgactgcc         1956
ccaaccagca ctcattttgc acagagcagg ggaatgatat ttgtcttgtg attttgacac        2016
tgacccagga aagtggctag tggatttaga ggaggtttat ctcagttttc cttattgagt        2076
cccccaacat tatcatcaaa cacttccctc tgtctctcct cccctagct ccaagaattc         2136
ccacctgtgg ctagctcctt ttatgcaccc agcacaggca ggtgtcaaga gaagtgctgc        2196
tggcattgtg gacggctggc ctccgtatgc ccctctctct gccttctggc ctccgtgtgc        2256
```

| | |
|---|---|
| cccctctctct gccttctggc cacgtggact tttgtgtctt ccgagaggtc tcatgccaga | 2316 |
| ccacatggtg acaacaggct tgagcctggg catggtgtcc atagcaatgc ttgttggctg | 2376 |
| ggcatgatgg ctcatgcctg caatcccagc acttcttggg aggccgagtc aggtggatca | 2436 |
| cttgagtcca ggagttcgag accagcctgg gcaacatatt gagaccctga ctctacaaaa | 2496 |
| aatacagaaa ttagccgggc gtggtggtgt gcacctatag tcccagctac tcggaggct | 2556 |
| gaggtgggaa gatcacttga acccagggga tggaggctgc agtaagctga gatggcgcca | 2616 |
| ctgcactcca gcctgggtga cagagcgaaa ccctgtctca aaaaacaaac aaacagaaaa | 2676 |
| cccaaaaagc caaaacaaaa cctgaaaccc ttgtcaagaa ggccattggg ctcatctcaa | 2736 |
| gctctagtcc actgaaggcc tgacctctga gtgttcctac tcgcggactc agggcctctg | 2796 |
| ttctctggtg tggtaatctg agttcctaat ttctatctta gctgaatgtt ctgccatgac | 2856 |
| cactgacacg tccaactcac atctctttgg agtcagtctc tttcctatcg aggtgggttt | 2916 |
| caggtcttgc ttgtggctca gtttccttgg cccaccttgt ggctgtcctc ctcccagctg | 2976 |
| ccaccagtcg ttcagtgtgg ccacgcagtt tttttgcaga aggcaggtga accacacctg | 3036 |
| ctcccatgct agcctcctct tccttttctc acctacccca gtgatttctt tgtgctctga | 3096 |
| gagacaagtt ccatgttctc catacaacct tctcattgtt gaagctcact tacgacctaa | 3156 |
| aacaattcga cgttggtaac gtgaggcagt ttgaggcagt gccctatcca gaatgcatgt | 3216 |
| cccatgggtc aaattaattt cagataacca aaaacttcat gtcccctgtg gttccttttg | 3276 |
| gggttgacgt tttgggggct gttttccatgt ctgacttggc accactgccc gacacgtagc | 3336 |
| tggaaaccat gacctatata taggcctgca ctgcccggca tttctttttgt tcttattctt | 3396 |
| ttacttggta aacacatttt tttttttcatt tacgtcggga tttctcagat tttgaagcat | 3456 |
| gagagggaga atgtatctat ttacaataat gaggaaaatt aagaatctta aatctttatg | 3516 |
| taaatcagta aacattcttt actaaccttt gatttattaa gaagtttctt ctgaatgaat | 3576 |
| aaagcacttt tgttattagt taaagca | 3603 |

<210> SEQ ID NO 2
<211> LENGTH: 425
<212> TYPE: PRT
<213> ORGANISM: Homo sapiens

<400> SEQUENCE: 2

Met Asp Ser Leu Val Thr Ala Asn Thr Lys Phe Cys Phe Asp Leu Phe
1               5                   10                  15

Gln Glu Ile Gly Lys Asp Asp Arg His Lys Asn Ile Phe Phe Ser Pro
            20                  25                  30

Leu Ser Leu Ser Ala Ala Leu Gly Met Val Arg Leu Gly Ala Arg Ser
        35                  40                  45

Asp Ser Ala His Gln Ile Asp Glu Val Leu His Phe Asn Glu Phe Ser
    50                  55                  60

Gln Asn Glu Ser Lys Glu Pro Asp Pro Cys Leu Lys Ser Asn Lys Gln
65                  70                  75                  80

Lys Val Leu Ala Asp Ser Ser Leu Glu Gly Gln Lys Lys Thr Thr Glu
                85                  90                  95

Pro Leu Asp Gln Gln Ala Gly Ser Leu Asn Asn Glu Ser Gly Leu Val
            100                 105                 110

Ser Cys Tyr Phe Gly Gln Leu Leu Ser Lys Leu Asp Arg Ile Lys Thr
        115                 120                 125

| | | | | | | | | | | | | |
|---|---|---|---|---|---|---|---|---|---|---|---|---|
| Asp | Tyr | Thr | Leu | Ser | Ile | Ala | Asn | Arg | Leu | Tyr | Gly | Glu | Gln | Glu | Phe |
| | 130 | | | | 135 | | | | | 140 | | | | | |

Asp Tyr Thr Leu Ser Ile Ala Asn Arg Leu Tyr Gly Glu Gln Glu Phe
          130                 135                 140

Pro Ile Cys Gln Glu Tyr Leu Asp Gly Val Ile Gln Phe Tyr His Thr
145                 150                 155                 160

Thr Ile Glu Ser Val Asp Phe Gln Lys Asn Pro Glu Lys Ser Arg Gln
                165                 170                 175

Glu Ile Asn Phe Trp Val Glu Cys Gln Ser Gln Gly Lys Ile Lys Glu
            180                 185                 190

Leu Phe Ser Lys Asp Ala Ile Asn Ala Glu Thr Val Leu Val Leu Val
                195                 200                 205

Asn Ala Val Tyr Phe Lys Ala Lys Trp Glu Thr Tyr Phe Asp His Glu
            210                 215                 220

Asn Thr Val Asp Ala Pro Phe Cys Leu Asn Ala Asn Glu Asn Lys Ser
225                 230                 235                 240

Val Lys Met Met Thr Gln Lys Gly Leu Tyr Arg Ile Gly Phe Ile Glu
                245                 250                 255

Glu Val Lys Ala Gln Ile Leu Glu Met Arg Tyr Thr Lys Gly Lys Leu
            260                 265                 270

Ser Met Phe Val Leu Leu Pro Ser His Ser Lys Asp Asn Leu Lys Gly
        275                 280                 285

Leu Glu Glu Leu Glu Arg Lys Ile Thr His Glu Lys Met Val Ala Trp
        290                 295                 300

Ser Ser Ser Glu Asn Met Ser Glu Glu Ser Val Val Leu Ser Phe Pro
305                 310                 315                 320

Arg Phe Thr Leu Glu Asp Ser Tyr Asp Leu Asn Ser Ile Leu Gln Asp
                325                 330                 335

Met Gly Ile Thr Asp Ile Phe Asp Glu Thr Arg Ala Asp Leu Thr Gly
            340                 345                 350

Ile Ser Pro Ser Pro Asn Leu Tyr Leu Ser Lys Ile Ile His Lys Thr
        355                 360                 365

Phe Val Glu Val Asp Glu Asn Gly Thr Gln Ala Ala Ala Ala Thr Gly
    370                 375                 380

Ala Val Val Ser Glu Arg Ser Leu Arg Ser Trp Val Glu Phe Asn Ala
385                 390                 395                 400

Asn His Pro Phe Leu Phe Phe Ile Arg His Asn Lys Thr Gln Thr Ile
            405                 410                 415

Leu Phe Tyr Gly Arg Val Cys Ser Pro
            420                 425

<210> SEQ ID NO 3
<211> LENGTH: 1275
<212> TYPE: DNA
<213> ORGANISM: Artificial Sequence
<220> FEATURE:
<223> OTHER INFORMATION: degenerate sequence
<221> NAME/KEY: misc_feature
<222> LOCATION: (1)...(1275)
<223> OTHER INFORMATION: n = A,T,C or G

<400> SEQUENCE: 3
atggaywsny tngtnacngc naayacnaar ttytgyttyg ayytnttyca rgarathggn     60
aargaygaym gncayaaraa yathttytty wsnccnytnw snytnwsngc ngcnytnggn    120
atggtnmgny tnggngcnmg nwsngaywsn gcncaycara thgaygargt nytncaytty    180
aaygarttyw sncaraayga rwsnaargar ccngayccnt gyytnaarws naayaarcar    240
aargtnytng cngaywsnws nytngarggn caraaraara cnacngarcc nytngaycar    300

-continued

```
cargcnggnw snytnaayaa ygarwsnggn ytngtnwsnt gytayttygg ncarytnytn    360
wsnaarytng aymgnathaa racngaytay acnytnwsna thgcnaaymg nytntayggn    420
garcargart tyccnathtg ycargartay ytngayggng tnathcartt ytaycayacn    480
acnathgarw sngtngaytt ycaraaraay ccngaraarw snmgncarga rathaaytty    540
tgggtngart gycarwsnca rggnaarath aargarytnt tywsnaarga ygcnathaay    600
gcngaracng tnytngtnyt ngtnaaygcn gtntayttya argcnaartg ggaracntay    660
ttygaycayg araayacngt ngaygcnccn ttytgyytna aygcnaayga raayaarwsn    720
gtnaaratga tgacncaraa rggnytntay mgnathggnt tyathgarga rgtnaargcn    780
carathytng aratgmgnta yacnaarggn aarytnwsna tgttygtnyt nytnccnwsn    840
caywsnaarg ayaayytnaa rggnytngar garytngarm gnaarathac ncaygaraar    900
atggtngcnt ggwsnwsnws ngaraayatg wsngargarw sngtngtnyt nwsnttyccn    960
mgnttyacny tngargayws ntaygayytn aaywsnathy tncargayat gggnathacn   1020
gayathttyg aygaracnmg ngcngayytn acnggnathw snccnwsncc naayytntay   1080
ytnwsnaara thathcayaa racnttygtn gargtngayg araayggnac ncargcngcn   1140
gcngcnacng gngcngtngt nwsngarmgn wsnytnmgnw sntgggtnga rttyaaygcn   1200
aaycayccnt tyytnttytt yathmgncay aayaaracnc aracnathyt nttytayggn   1260
mgngtntgyw snccn                                                    1275

<210> SEQ ID NO 4
<211> LENGTH: 6
<212> TYPE: PRT
<213> ORGANISM: Artificial Sequence
<220> FEATURE:
<223> OTHER INFORMATION: peptide tag

<400> SEQUENCE: 4

Glu Tyr Met Pro Met Glu
 1               5

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer ZC38,167

<400> SEQUENCE: 5
tgagtattgc caacaggctt tatg                                            24

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer ZC38,168

<400> SEQUENCE: 6
agagtccttt tggcgtcatc at                                              22
```